(12) United States Patent
Wu

(10) Patent No.: US 8,283,169 B1
(45) Date of Patent: Oct. 9, 2012

(54) DIFFERENTIAL GRADIENT SEPARATION OF CELLS

(76) Inventor: Allan Yang Wu, Cathedral City, CA (US)

(*) Notice: Subject to any disclaimer, the term of this patent is extended or adjusted under 35 U.S.C. 154(b) by 1160 days.

(21) Appl. No.: 12/074,916

(22) Filed: Mar. 8, 2008

Related U.S. Application Data

(60) Provisional application No. 60/919,293, filed on Mar. 21, 2007.

(51) Int. Cl.
| | |
|---|---|
| *C12N 5/02* | (2006.01) |
| *A61K 35/12* | (2006.01) |
| *G01N 33/53* | (2006.01) |
| *G01N 33/543* | (2006.01) |
| *G01N 33/545* | (2006.01) |

(52) U.S. Cl. ......... 435/378; 435/7.1; 435/325; 424/574; 436/501; 436/518; 436/531; 436/824

(58) Field of Classification Search .................. None
See application file for complete search history.

(56) References Cited

U.S. PATENT DOCUMENTS

| | | | | |
|---|---|---|---|---|
| 4,301,139 A | * | 11/1981 | Feingers et al. | ............... 436/500 |
| 4,714,680 A | | 12/1987 | Civin et al. | |
| 5,215,926 A | * | 6/1993 | Etchells et al. | ............... 436/501 |
| 5,409,833 A | | 4/1995 | Hu et al. | |
| 5,610,074 A | | 3/1997 | Beritashvili | |
| 5,773,574 A | * | 6/1998 | Ginsberg et al. | ............... 530/327 |
| 5,786,207 A | | 7/1998 | Katz | |
| 6,200,606 B1 | | 3/2001 | Peterson et al. | |
| 6,316,247 B1 | | 11/2001 | Katz et al. | |
| 7,001,746 B1 | | 2/2006 | Halvorsen et al. | |

OTHER PUBLICATIONS

Kotaro Yoshimura; Tomokuni Shigeura; Daisuke Matsumoto; Takahiro Sato; Yasuyuki Takaki; Emiko Aiba-Kojima; Katsujiro Sato "Characterization of Freshly Isolated and Cultured Cells Derived from the Fatty and Fluid Portions of Liposuction Aspirates", J. Cellular Physiology, Mar. 23, 2006, 208(1), pp. 64-76.*
Vida et al "Lipoinjection", Vida Skin and Cosmetic Surgery, <url:http://www.liporevolution.com/about_drvida.asp>, accesed online Aug. 10, 2011, 4 pages.*
Kitagawa, M., Miyazaki., T., Kobori, M., Omae, K., Takamatsu, S., "Cell-assisted lipotransfer (CAL): supportive use of human adipose-derived cells for soft tissue augmentation with lipoinjection," Cosmetic Medicine in Japan, Jan. 2007, 9 pages.
Zuk, P.A., Zhu, M., Mizuno, H., Huang, J., Futrell, J.W., Katz, A.J., Benhaim, P., Lorenz, H.P., and Hedrick, M.H."Multilineage cells from human adipose tissue: implications for cell-based therapies," Tissue Engineering, 2001, 7 (2) ,pp. 211-228.

\* cited by examiner

*Primary Examiner* — Chris R Tate
*Assistant Examiner* — Aaron J Kosar
(74) *Attorney, Agent, or Firm* — Biotech Beach Law Group PC

(57) ABSTRACT

A device and method in which cells of a heterogeneous population are separated through a column partially packed with antibody coated beads. The antibody coated beads may be placed in a gradient fashion such that each layer binds to and selects a subset of cells from the entire sample population. A lipoaspirate fluid, or other fluid containing cells, may be brought through the column by positive pressure on the specimen bag side and negative pressure at the base of the column with a vacuum line and waste trap. The column may then be inverted and irrigated internally with a wash buffer to remove unhomogenized macroscopic tissue material and unbound residual cells. The column may be closed at the ends and shaken and/or washed with an enzymatic buffer. Cells may be removed from the device with an elution buffer.

5 Claims, 8 Drawing Sheets

DIFFERENTIAL GRADIENT SEPARATION OF CELLS

CROSS-REFERENCE TO RELATED APPLICATION

This application claims the benefit of U.S. Provisional Patent Application No. 60/919,293 filed Mar. 21, 2007; this provisional application is incorporated herein by reference in its entirety.

FIELD OF THE INVENTION

The present invention relates to a device and method for separation of cells from a heterogeneous population. In one exemplary application, the population may be derived from liposuction adipose tissue.

BACKGROUND OF THE INVENTION

Liposuction is a surgical technique using instruments to remove unwanted fatty tissue in a minimally invasive fashion from humans or animals. Typically liposuction is carried out with a tumescent fluid to allow improved anesthesia and minimal blood loss. The waste fluid and fatty tissue is commonly discarded, although sometimes the adipose tissue may be reclaimed and transplanted back into the patient for aesthetic, cosmetic or other therapeutic reasons.

Adipose tissue transfer, however, has been fraught with difficulties in that loss of volume and even necrosis to the transposed fat may occur; either result yielding aesthetically unappealing results and the necessity for repetitive treatments or treatments with an alternate material or dermal filler. Successful fat transfer in the nude mouse model with human tissue has been confirmed by Kitagawa and Takamatsu when transferring adipose cells with a partially purified mixture of adult stem cells isolated from the original lipoaspirate tissue and fluid (Takamatsu 2006). Others have hypothesized that these adipose derived stem cells also carry other therapeutic uses and have devised methods of isolating them (Halvortsen 2006).

One method and system, made by the Cytori corporation, uses a series of enzymatic buffers and washing agents in combination with a modified centrifugation system to isolate the stromal vascular fraction of liposuction waste (Zuk 2001). The stromal vascular fraction is enriched with adipose stem cells in addition to other cells. This fraction may then be used for further culture, isolation and/or manipulation of pure stem cells for further cellular therapies. Although the Cytori device is able to isolate stem cells in a facile fashion, the cost of the modified centrifugation system is prohibitively expensive and is composed of moving parts which invariably will require maintenance. Furthermore the centrifugation method is not capable of directly isolating and selecting specific cells expressing antigen markers of clinical interest. Other devices such as those mentioned in U.S. Pat. Nos. 5,409,833, 5,610,074, 5,786,207 and 6,316,247 though economical are still unable to selectively remove specific subsets of cells from the entire liposuction fluid milieu. This is concerning as stem cells do have the potential of becoming any type of tissue including possibly even malignant tissue or tissue that is inappropriate for the site of transfer. For example, if adipose derived stem cells were transferred to a soft tissue area such as the lips, specific stem cells ultimately destined for bone production would lead to hardening of the intended area of treatment. Therefore, an alternate method and apparatus less costly and having greater specificity of isolating clinically relevant cells would be of both clinical and commercial relevance.

SUMMARY OF THE INVENTION

An embodiment of the invention includes a modified immobilized sterile column packed with different layers of antibodies immobilized on methylcellulose beads. Antibodies employed in this method may be arranged such that the constant region of the antibody is bound directly to the bead allowing the recognition binding site for the antigen to be facing outward and away from the bead. This allows cells expressing the specific antigen of interest, to bind to the antibody and ultimately become immobilized on the bead. The very top and bottom of the column may be capped with adjustable ports that may be opened and closed to regulate the flow of fluid in and out of bead layers. Within each antibody-bead layer the antibodies bind to the same antigen and can isolate the same type of cell from the sample population. Between different layers the antibodies bind to different cell subsets. The order of the layer is determined by pre-testing or having prior knowledge of relative percentages of desired cell subsets. This can be done by flow cytometry or a cell counter. A layer that will bind commonly occurring cells may be placed at the bottom of the column, whereas a layer binding to successively less populous cells may be placed in the next level above the last, such that the entire column may reach saturation of cell binding from the base of the column upward to allow free flow of the entire specimen fluid. For example, if the layer binding to the most populous cell is placed at the top of the column, it would be quickly saturated and clogged with cells and debris such that sample fluid will never flow through subsequent antibody layers. Therefore it can be more efficient for the apparatus to bind the least commonly occurring cells towards the top of the column and the more common cells toward the bottom. This allows for a single pass effect in which the sample requires being run through the column only once to isolate different cell types.

Liposuction fluid flow may be further or completely facilitated with positive pressure on the specimen bag and negative pressure in the form of a vacuum receptacle at the base of the column. The liposuction fluid may also be processed with enzymes to detach vital cells from the tissue and fatty matrix to improve cell yield.

Once the liposuction fluid has completely run through, the column may be closed at the ports, inverted and reopened and reconnected to a washer buffer at the top of the column and a vacuum waste receptacle at the bottom. After all residual cellular debris has been removed; the cells may then either mechanically (by gentle agitation or rocking of the column) or enzymatically cleaved from the antibody beads. The column may then be connected to a collection tube or syringe and eluted out in any suitable media or buffer for clinical or laboratory use.

An illustration using the invention described involves using the device to purify cells with CD31, CD34 and CD144 antigen expression from processed or unprocessed liposuction fluid. The layers of the antibody bead column may be arranged in such a manner to allow the most common cells (CD34) in the population to be at the very bottom, whereas the antibody beads to the more rare cells (CD144 and CD31) can be placed at the top of the column. In this way the higher layer of beads do not become immediately saturated and clogged causing nonspecific cell to cell binding in the column and ultimately impeding fluid flow prematurely before all specimen has flowed though.

In one embodiment of the invention, cells passing through the column come in contact with the methylcellulose beads thereby starting the process of favorable cellular differentiation. In other embodiments of the invention, other suitable bead material and sizes may be utilized to affect an alternate form of differentiation. Cells may be mixed with different ratios of adipose tissue and transferred back to the patient as a dermal filler or for other therapeutic uses.

The process using the device described herein may be carried out at any suitable temperature, as the entire apparatus may be encased in a controlled thermal barrier. Also, cells obtained from the process or device described herein may be added to any suitable material, graft and/or other vital fractions of tissue, such as adipose tissue, for implantation into animals or humans.

Those familiar with the art and field of cellular and molecular biology and medicine are aware the invention and all potential embodiments may be modified and composed of alternate materials to enhance or improve the process of selection and isolation or clinical outcomes and/or laboratory applications. Similarly, a method of using the apparatus may include a variety of different steps.

DETAILED DESCRIPTION

Figure 1:
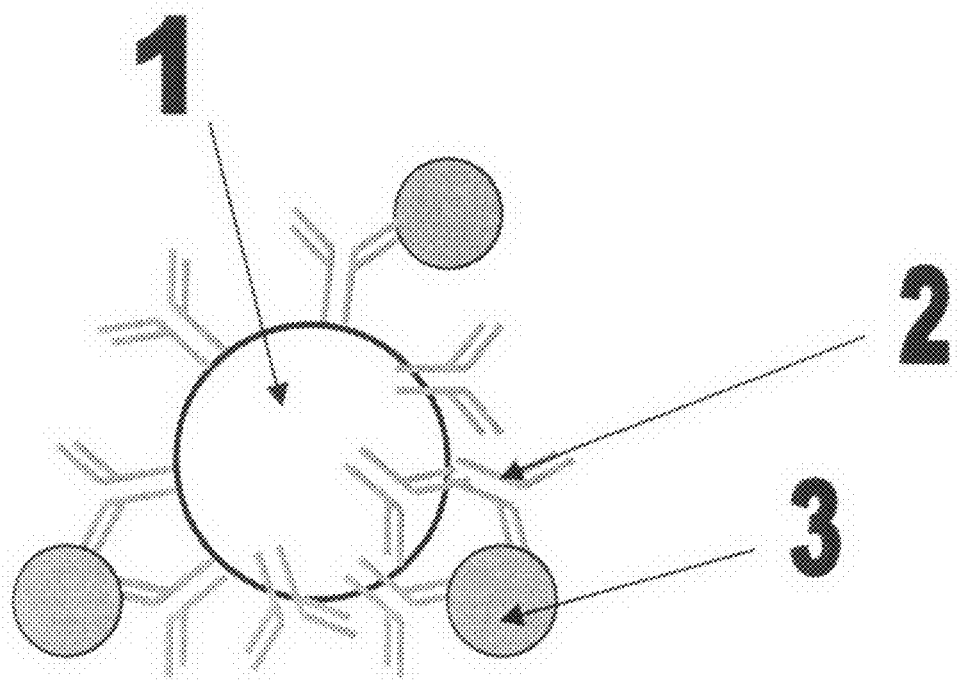
FIG. 1: A highly magnified conceptual drawing depicting the smallest functional unit of the device, an antibody coated methylcellulose bead.

FIG. 1 illustrates a highly magnified conceptual drawing of the smallest functional unit of the device, the antibody 2 coated methylcellulose bead 1. Note how the variable chain fragments of the antibody 2 that bind to the antigen on the cells of interest 3 are oriented radially away from the surface of the bead.

Figure 2:
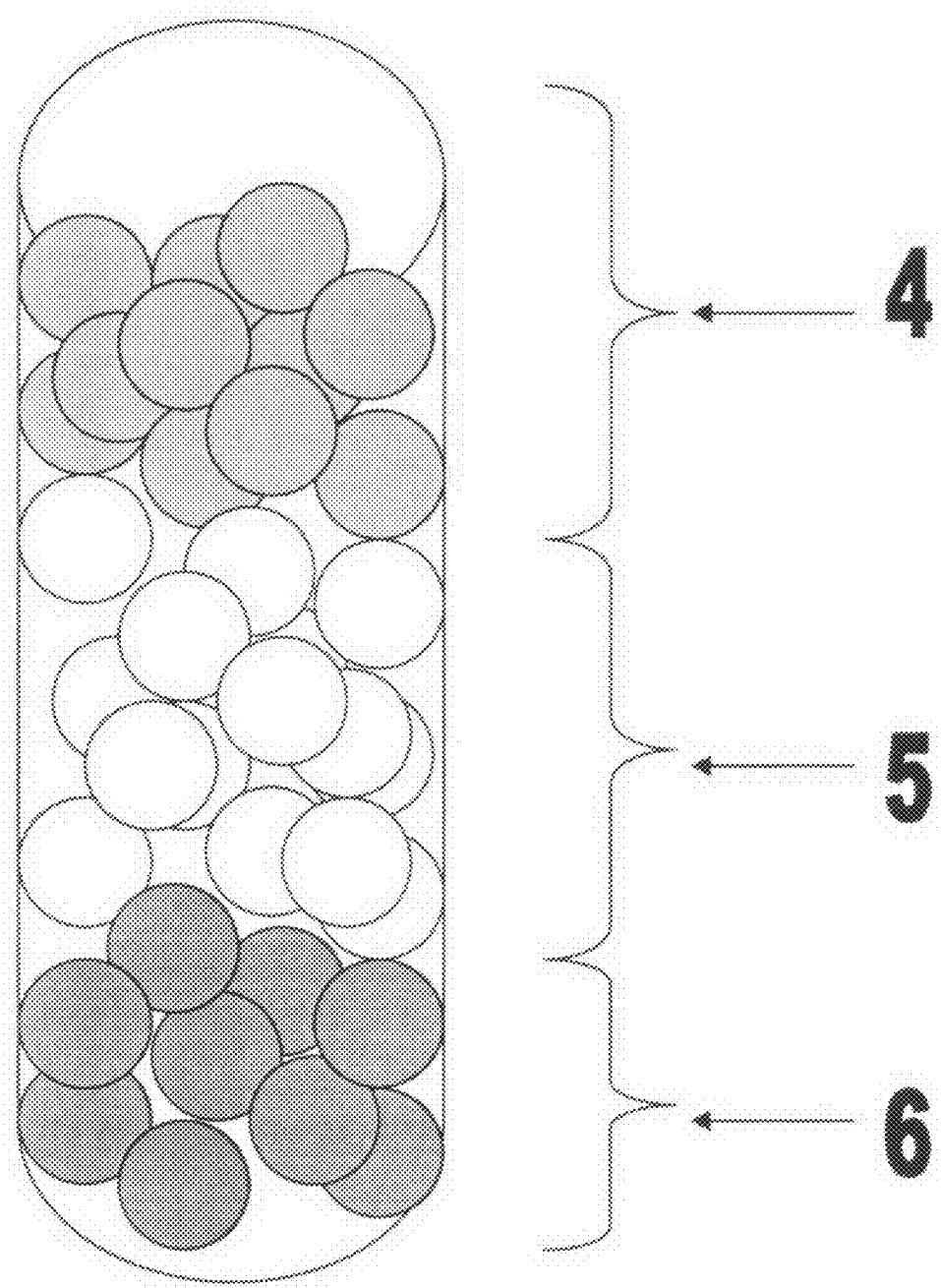
FIG. 2: A conceptual drawing of the antibody-bead column depicting the stratified layers as different colors.

FIG. 2 illustrates a conceptual drawing of the antibody-bead column depicting stratified layers 4, 5, and 6. While the embodiment in FIG. 2 shows three stratified layers, a person of ordinary skill in the art would appreciate that any number of stratified layers may be used. For example, the column may contain one layer or even hundreds of layers of beads. The layers may not be perfectly separated; the layers may in fact comprise a gradual change from one type of bead to another. Some beads within the layers may be mixed up; for example, this may occur to some degree when fluid passes over the beads or from natural mixing of some beads.

A variety of embodiments of the apparatus for isolating specific cell subsets from a total heterogeneous population of sample cells are possible. The apparatus may comprise a specimen line, a bead column, the bead column containing beads coated with antibodies, and a waste line. The specimen line and waste line may be connected to a bead column. The apparatus may optionally allow the column to be enclosed in a thermally controlled housing. Optionally, the thermally controlled housing may be reusable and the antibody-bead column afferent and efferent lines may be optionally disposable. Optionally, the bead column may contain a plurality of layers of beads and each layer may contain beads coated with antibodies specific to just one type of antigen.

A variety of embodiments of the bead column are possible. For example, the bead column may optionally contain an afferent and efferent port, the afferent and efferent ports may be adjustably closable. The base of the column may be optionally attached to a vacuum trap and receptacle to collect fluid and cells flowing out of the column base. A specimen bag may optionally be connected to the antibody column and the column may be pressurized by compression applied to the specimen bag. Also, optionally, filter column layers may be physically divided into separate but communicating chambers, each chamber capable of emptying beads.

Optionally, the column may further comprise separate spill ports at each layer in case lower levels become clogged or saturated prior to processing all fluid specimen.

A variety of beads or particles may be used in the column. The beads may comprise means for increasing purification of the sample cells and means for enhancing favorable differentiation. The beads may be of a variety of sizes. For example, the beads may be within a range of 10 microns to 10 cm in diameter and the beads may be coated with antibodies. In one embodiment, the antigen binding sites are oriented away from the surface of the bead. The beads may be composed or coated with any one of the following group: methylcellulose, sepharose, agarose, gelatin, chitin, IGF-1, VEGF, bFGF or any other suitable material known to a person of ordinary skill in the art. Optionally, the beads may comprise antibodies to CD31, CD 144 or CD34 or the beads may comprise other antibodies known to a person of ordinary skill in the art. The antibodies immobilized on the beads may be at least any one of the following: anti-mouse, anti-goat, anti-horse, anti-bovine, anti-monkey, anti-rat, anti-human, or anti-rabbit. Optionally, in an embodiment involving a vertical (or near vertical) column, the beads coated with the least commonly binding antibodies may be placed in the top layer, and beads coated with antibodies that bind to cells that predominate in the sample fluid may be placed in a bottom layer. Also, some or all beads may not be coated with antibodies. This kind of filler bead may be used to more evenly distribute the flow of sample through the specimen so that saturated binding beads have space between them. In another embodiment, the beads or antibodies may have magnetic or paramagnetic properties. The fluids passing through the column may also have magnetic or paramagnetic properties. Also optionally, the beads may contain pores. For example, pores may range from 10 microns to 2 centimeters to facilitate enhanced purification of selected cells.

Figure 3:
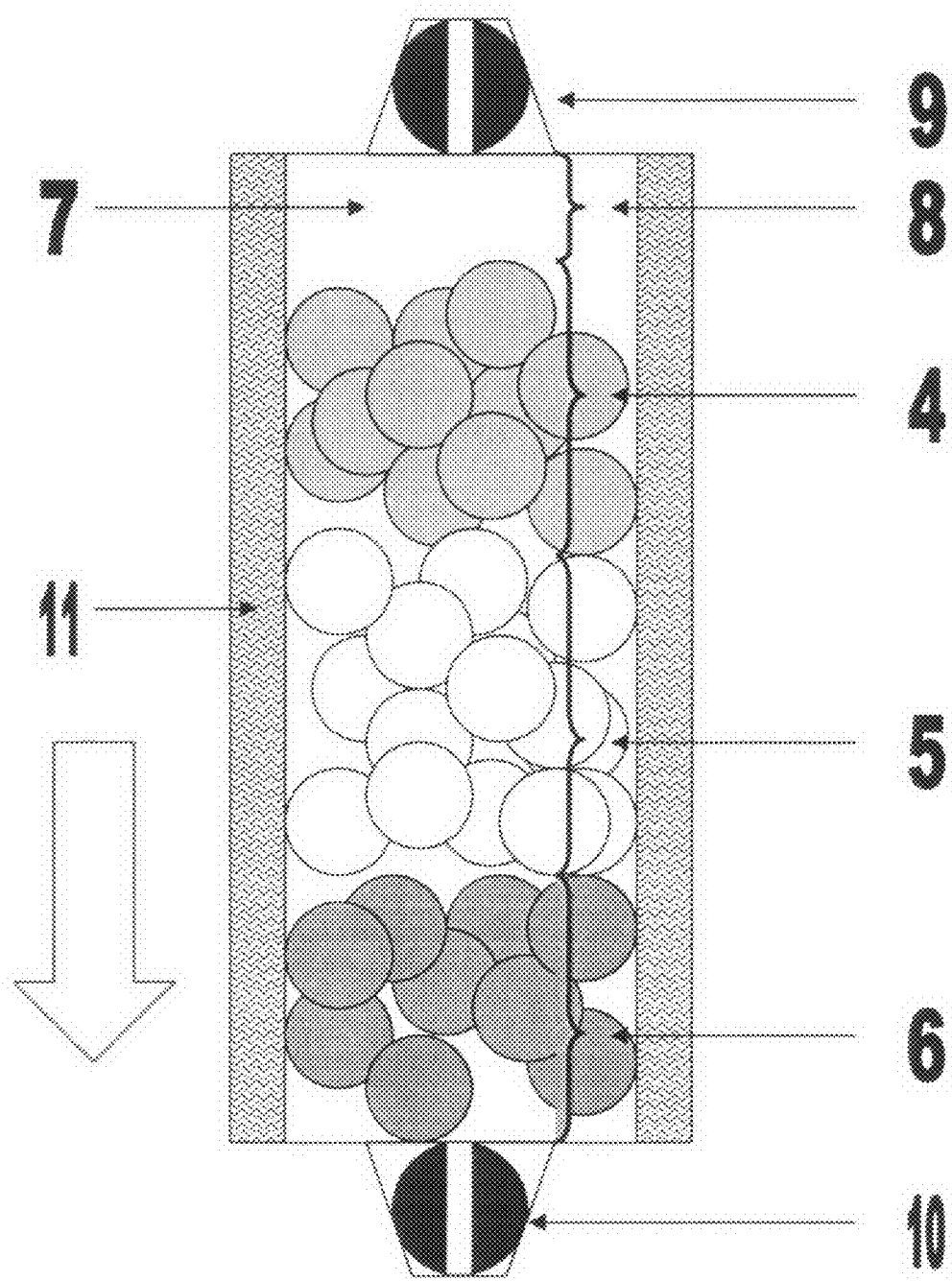
FIG. 3: A detailed drawing of the antibody-bead column during sample loading and first wash step.

FIG. 3 illustrates a cross-sectional drawing of an antibody-bead column 7 during sample loading and first wash step. A large arrow adjacent to the column depicts direction of sample flow. Adjustable ports 9 and 10 may be used to open and close the column 7. The column 7 and the entire apparatus may be wrapped in a thermally controlled housing 11 as represented in herringbone patterned fill in. Empty space 8 above the bead layer 4, 5 and 6 may facilitate specimen flow and allow mechanical detachment depicted in FIG. 5. In this configuration the sample fluid enters through the top port 9 of the column 7 and flows through the layers 4, 5 and 6 to bind out and select cells of interest and ultimately drains out the base port 10. Base port 10 may be connected to a vacuum to facilitate fluid pull through. A wash step may be performed in this configuration as well to remove nonspecific binding of cells in addition to removing tumescent fluid additives (such as lidocaine and epinephrine) used for liposuction.

Figure 4:
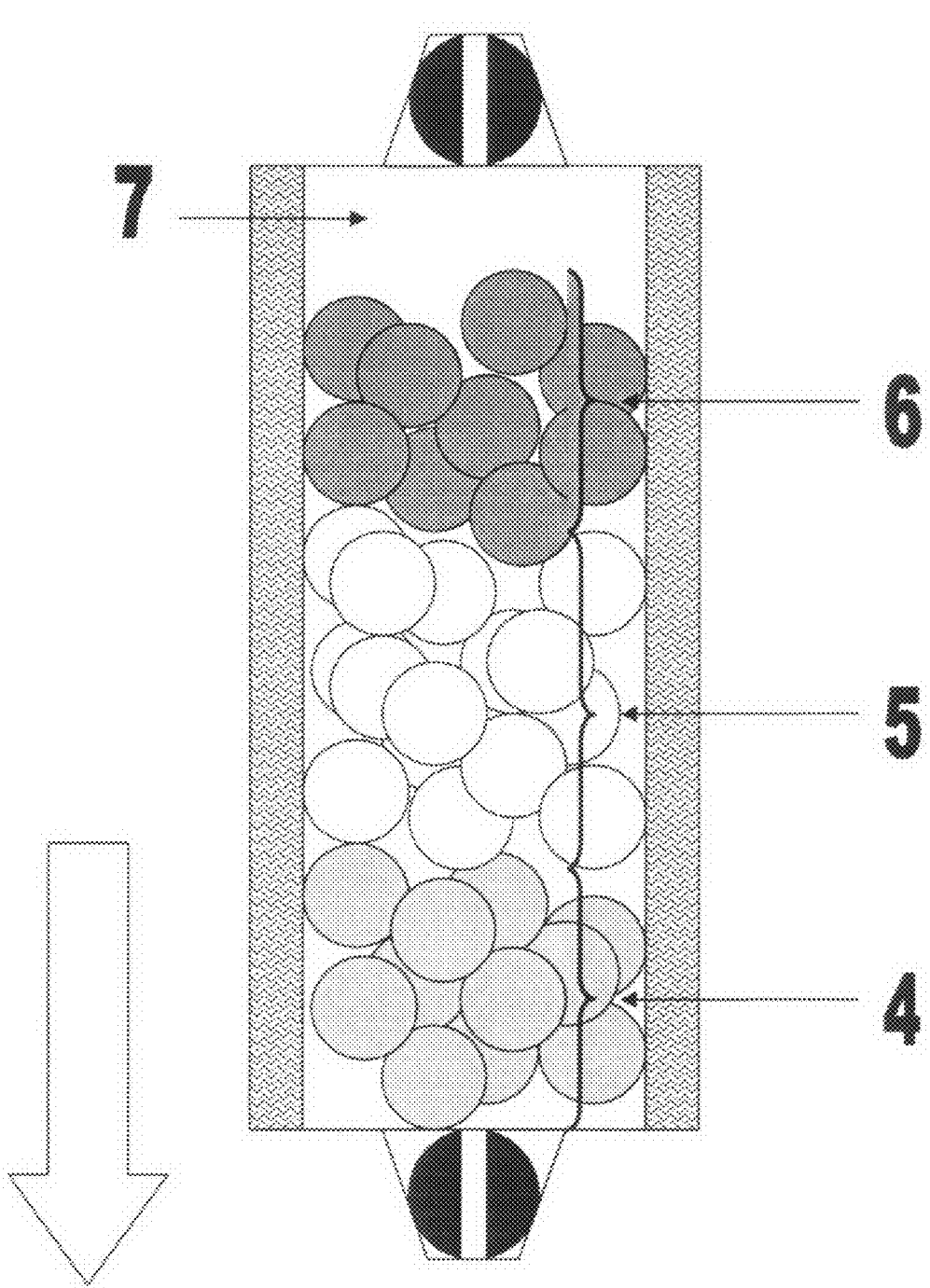
FIG. 4: A detailed drawing of the antibody-bead column inverted during the second wash step.

FIG. 4 depicts a detailed cross-sectional drawing of the antibody-bead column 7 inverted to undergo a second wash step. Thicker tissue remnants trapped in the now lower layer 4 can more easily be eluted with a washing buffer. Open arrow adjacent to bead column 7 indicates direction of buffer flow.

Figure 5:
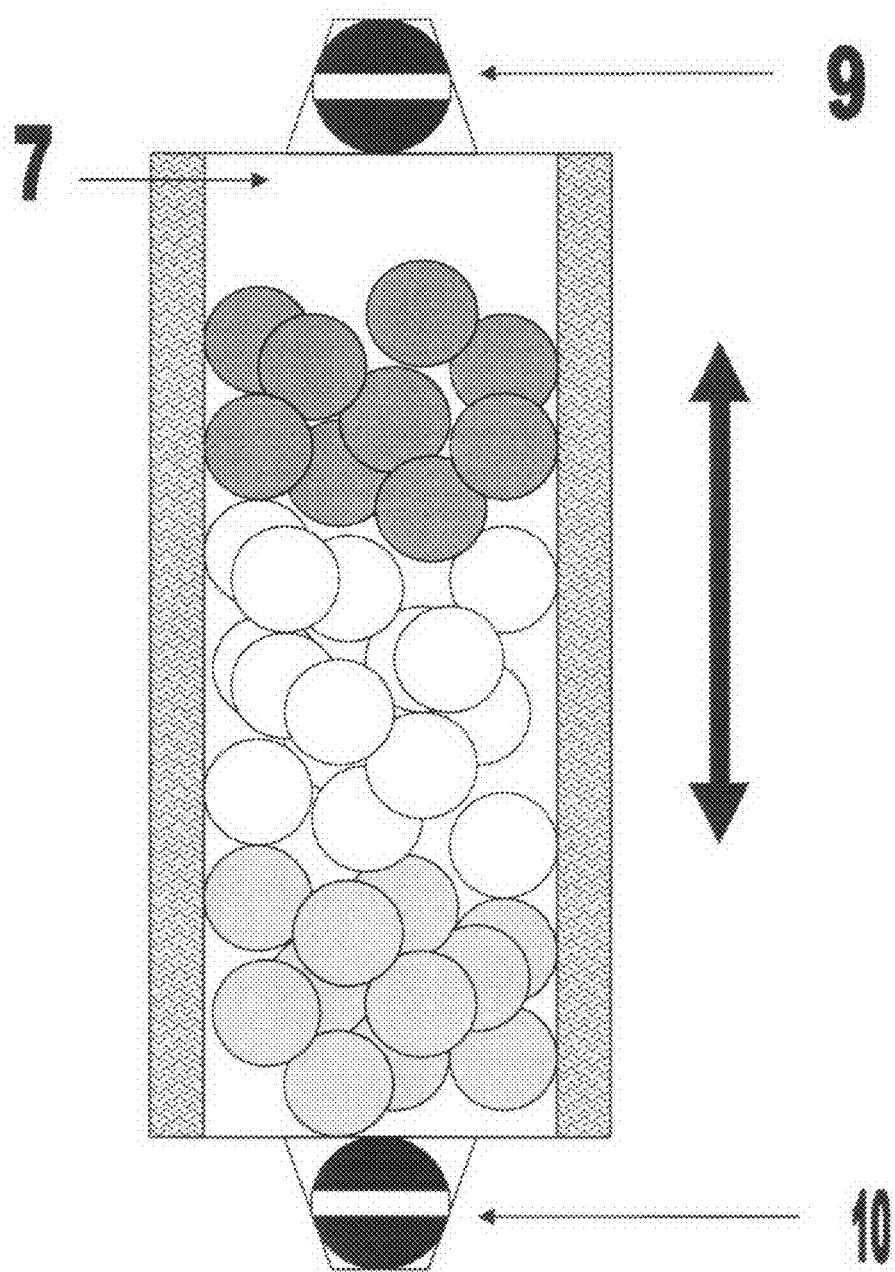
FIG. 5: A detailed drawing of the antibody-bead column during detachment step with both ports closed. The entire column is shaken to mechanically detach the cells from the beads.

FIG. 5 illustrates a detailed cross sectional drawing of the antibody-bead column 7 during detachment step with both ports 9 and 10 closed. The entire column 7 is shaken in the axis depicted by the double arrow to mechanically detach the cells from the beads. Elution buffer, media or enzymatic solution for suspension or cleavage from beads can be added to the column 7 at this time prior to closure of the ports 9 and 10.

Figure 6:
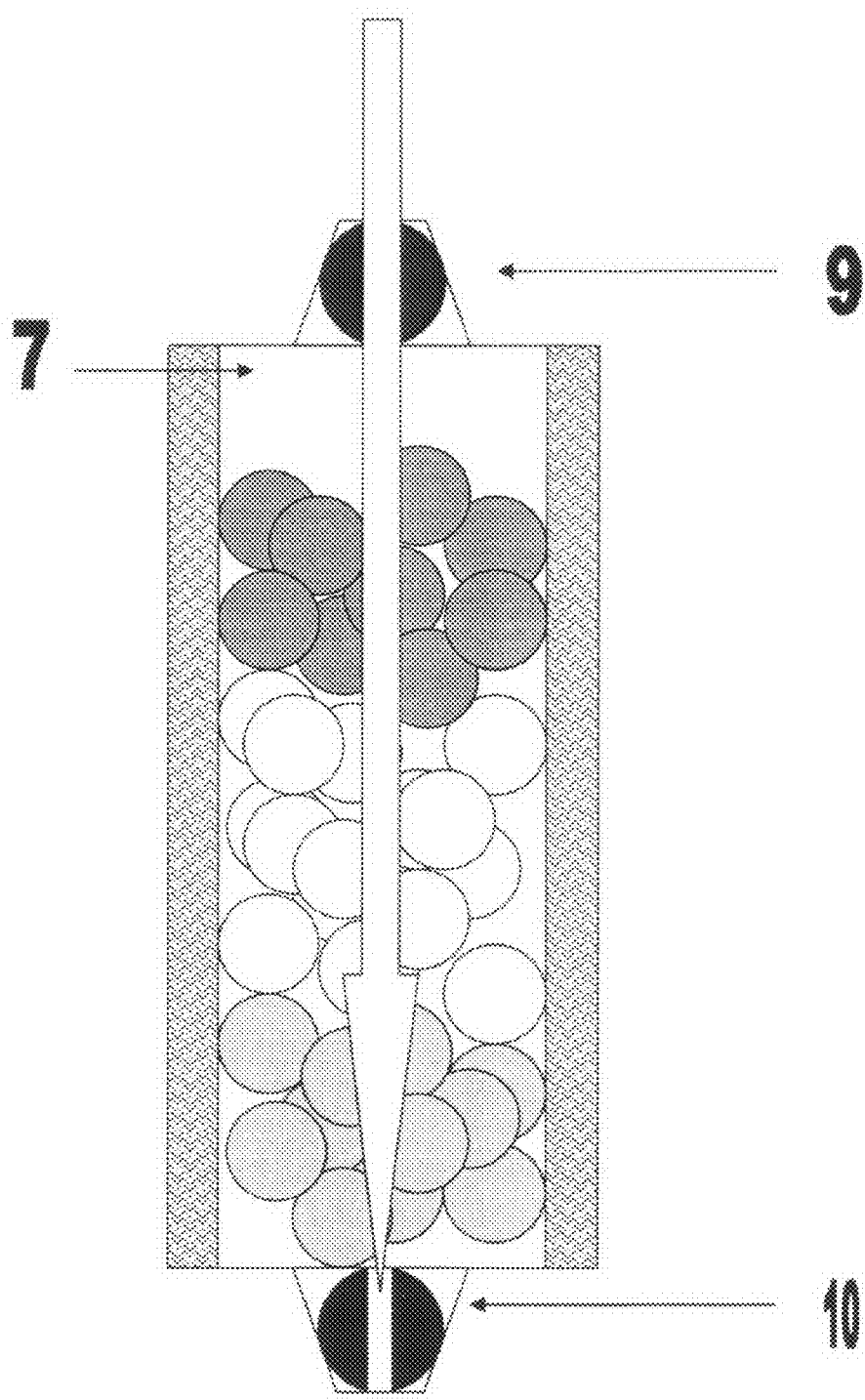
FIG. 6: A conceptual drawing indicating final elution step.

FIG. 6 illustrates a conceptual drawing indicating final elution step where the column 7 is opened at the ports 9 and 10 and final elution buffer is run through the column as depicted by the open arrow out of the bottom port 10 into a suitable container.

Figure 7:
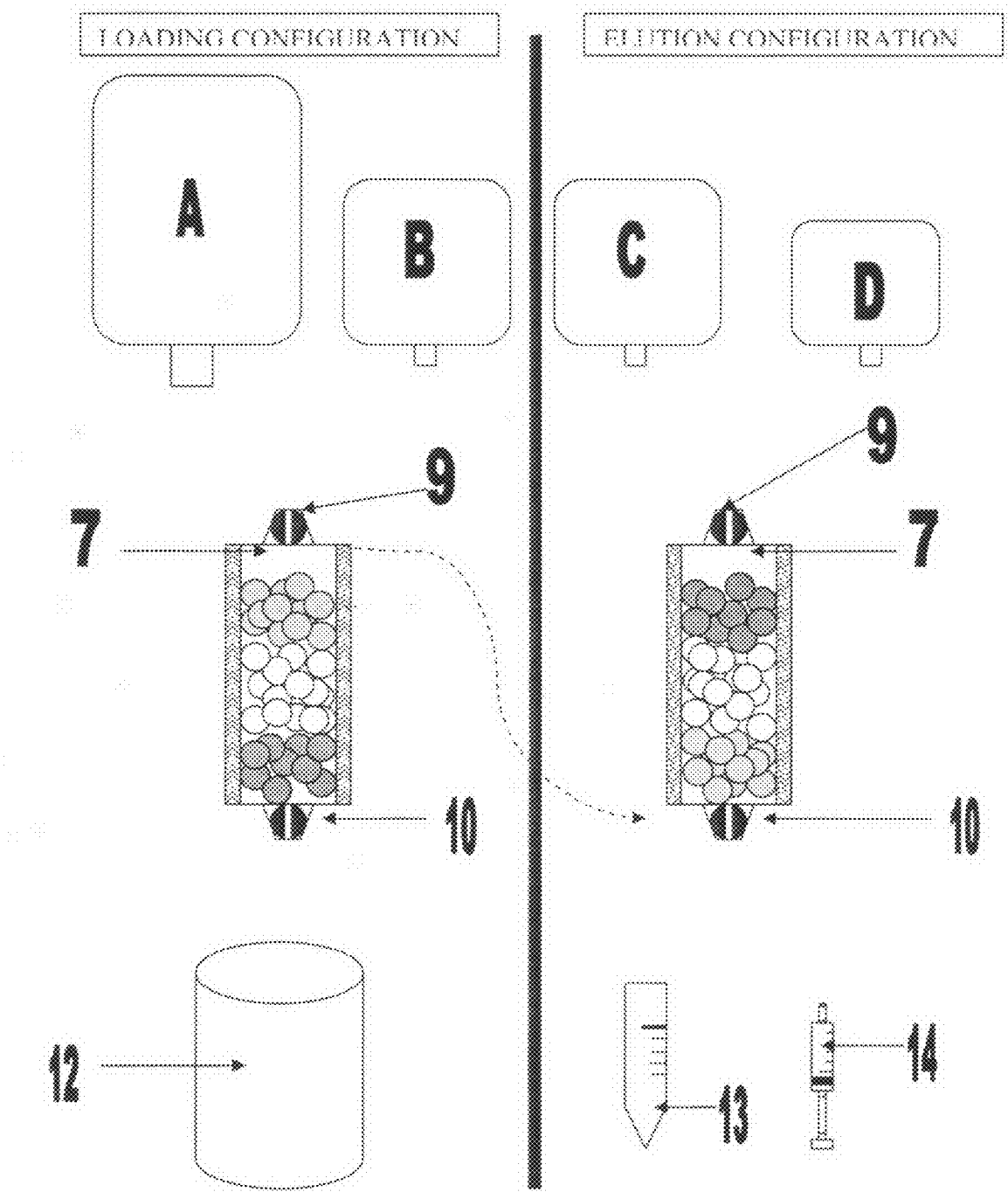
FIG. 7: An overall conceptual drawing of the apparatus in the clinical setting showing all necessary functional components.

FIG. 7 depicts an overall conceptual drawing of apparatus in the clinical setting. The drawing shows how the device could actually be deployed in a clinical setting where fluid bags, similar to IV fluid bags, contain liposuction fluid A, washing buffers B and C, and elution buffer D. Bag A contains lipsuction fluid A, bags B and C contain buffers B and C and bag D contains buffer D.

The binding phase of the procedure is depicted to the left of the vertical centerline. During this phase bag A is attached to the column 7 top port 9 by any suitable tubing (preferably non-adherent to cells). The bottom port 10 is connected to a vacuum trap or waste receptacle 12. After a substantial amount of the sample has run through the column, bag A is detached and bag B is connected to the top port 9 for the wash step. Once the first wash buffer has run out of the column 7, the entire column 7 is inverted (depicted by curved dotted line) to the elution configuration and then reconnected to the next wash buffer bag C at the top port 9 and the bottom port is again connected to the vacuum/waste receptacle 12. After final washing buffer C is run through, the column can then be closed at the ports 9 and 10 and shaken vigorously to detach cells. (Not shown in this diagram.) Alternatively the column can be filled with enzyme solutions or media prior to the ports being closed. (Not shown in this diagram.) Finally an elution buffer in bag D can be used to flush out all detached cells into any suitable receptacle such as a conical centrifuge tube 13 or syringe 14 for clinical and/or laboratory use.

Variations of methods in which fluid and tissue is processed to isolate specific cell subsets from a total heterogeneous population of sample cells are possible. While at least one method of use of the apparatus has been described, a person of ordinary skill in the art can see that a variety of steps may be used with the column and it is possible to add or remove optional steps to the method. The method may comprise applying a sample fluid to an opening on a column, the column containing one or more layers of beads, the beads coated with antibodies. The method may include allowing some of the sample fluid to pass through the column or over the beads. The user may apply an elution buffer, media or enzymatic solution to an opening on the column, and pass some of the elution buffer, media or enzymatic solution through the column. The user of the apparatus may collect any amount of elution buffer, media or enzymatic solution.

The method may further comprise optional wash steps. After allowing a substantial amount of the sample fluid to pass through the column, the method may include applying a first wash buffer to an opening on the column and after allowing some of the first wash buffer to pass through the column, the method may also comprise applying a second wash buffer to an opening on the column and allowing some of the second wash buffer to pass through the column. Any number of wash steps may be performed when using the method.

The method may also optionally comprise determining the number of layers within the column and determining the order of layers of beads within the column. For example, a user may test the sample fluid with flow cytometry in order to determine approximate percentages of the population for each cell of interest. The number of layers may be determined by the specific cell populations of interest. For example if there are cell types A, B, C and D and there is only interest in collecting B and C, then the apparatus may be setup with 2 layers of beads. Following the example, if B comprises approximately 75% of the population and C makes up approximately 5%, then the layer of beads collecting B may be stacked below the layer collecting C in order to reduce clogging within the column. In other words, the beads that collect the higher percentage of cells may be stacked lower. Though the number and order of layers may be determined and set in order to reduce clogging within the column, the number and order of the layers to use in the column is optional.

The method may optionally comprise inverting the column after allowing some of the sample fluid to run through the column. While use of gravity is one means to cause fluid to pass through the column, one or more pumps or other device to create pressure may be used to move fluid through the column. Another optional step could be to reverse pressure by a pump such that fluid runs in the other direction. Notably, an embodiment of the invention that has the column aligned in a substantially horizontal direction may use one or more pumps to modify the pressure on either side of the column in order to move fluid through the column in any direction. Depending on the method used to cause fluid to move through the column, the column may be aligned in any direction.

The method may optionally further comprise closing openings on the bead column and agitating the column to mechanically detach some cells from the beads. The column may be agitated manually or the column may be agitated using mechanical vibration created by other suitable means, such as by a shaker or other device.

The method may optionally comprise applying a buffer containing an enzyme to an opening on the column wherein the enzyme cleaves the cells bound to the beads. The enzyme may be used to extract the cells bound to the beads.

The method may optionally further comprise washing the beads in an electrolyte and collecting cells from the beads with a magnetic field.

The method may optionally further comprise collecting unwanted cells within the column and collecting desired cells within the elution buffer, media or enzymatic solution.

In a further embodiment the apparatus and method may be used with other biologic fluid specimens and other animal species.

Figure 8:
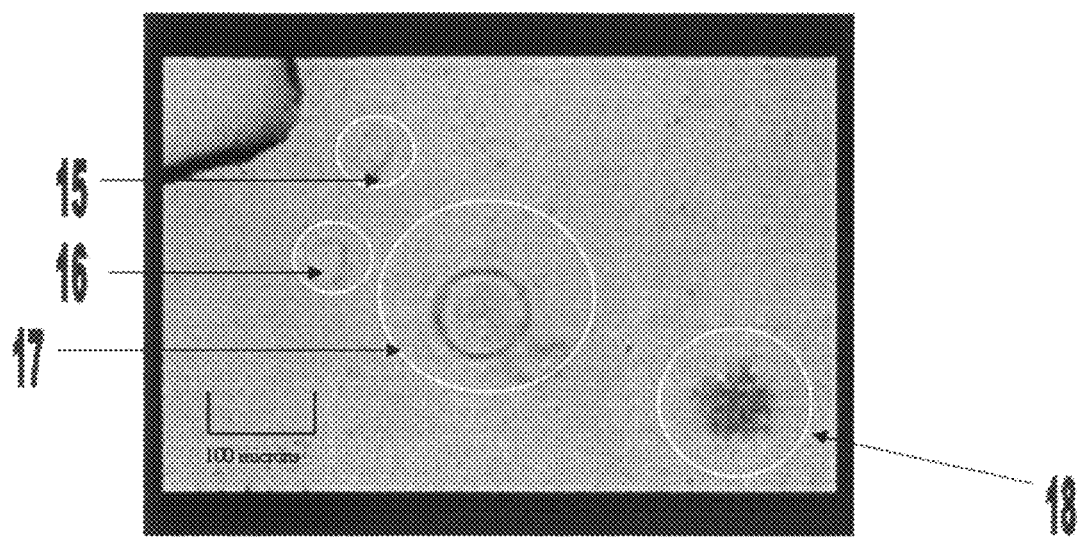
FIG. 8: A picture of a CD34 cell and smaller cluster of CD144 cells, with immunoperoxidase staining, isolated with a gradient, antibody-bead column.

FIG. 8 is a picture of resulting cells after use of a method involving two wash steps with an embodiment of the apparatus described herein. FIG. 8 demonstrates successful results from use of the apparatus. FIG. 8 shows a CD34 cell 17 and smaller cluster of CD144 cells 15, 16, 18, with immunoperoxidase staining, isolated with a gradient antibody-bead column. In this example, column beads were prepared by coating 5 mm agarose beads with avidin. Antibodies (either CD34 or CD144 polyclonal) were biotinylated and then conjugated to the avidin bead surface coat. Original adipose specimen was digested with collagenase enzymes then run through a gradient column composed of two layers: CD144 antibodies as the uppermost layer and CD34 at the bottom layer. Column was washed once with 500 cc of phosphate buffer solution (PBS), then inverted and further irrigated with another 500 cc of PBS. Column was then sealed at the ends and shaken on the vertical axis for 1 minute and 10 cc of Hams F-12 media was added to the interior of the column and closed once again. Column was then shaken on the vertical axis for another minute. Column ports were opened to allow drainage of cells and media out the base into a 15 mL conical centrifuge tube. Cells were concentrated down by centrifuging at 300 g for 10 min. Pellets were re-suspended in 1000 uL of PBS. Cells were then stained with 1 uL of monoclonal mouse CD34 and CD144 antibodies followed by staining with rabbit anti-mouse polyclonal antibodies and stained by immunoperoxidase reaction. Cells were visualized with a Nikon Diaphot 300 inverted microscope camera under 40× magnification.

I claim:

1. A method of forming a cell subset enriched dermal filler for a subject in need thereof, the method comprising:
   a) harvesting adipose fluid and tissue from a subject by liposuctioning said subject, thereby obtaining a harvested sample containing said adipose fluid and tissue;
   b) pre-testing the harvested sample, comprising determining from a first portion of the harvested sample a relative percentage of CD31, CD144, or CD34 cell subsets in the harvested sample;
   c) providing a chromatographic column having cell capture layers, wherein each cell capture layer is capable of capturing a cell of the cell subsets and each layer is provided in a cell capturing amount proportional to the determined relative percentage of step b);
   d) applying the harvested sample or a second portion thereof to the column to capture the cell subsets from the harvested sample or the second portion thereof, thereby providing a bound cell-captured sample portion and an unbound sample portion;
   e) discarding the unbound sample portion from the column;
   f) eluting the cell subsets of the bound cell-captured sample from the column, thereby collecting an isolate containing the cell subsets; and
   g) mixing the cell subsets isolate with adipose tissue thereby forming said cell subset enriched dermal filler.

2. The method of claim 1, further comprising after steps d) or e), washing the column with two or more wash buffers.

3. The method of claim 1, wherein the cell capture layers are ordered such that cells of more abundant cell subsets are captured below cells of less abundant cell subsets.

4. The method of claim 1, further comprising applying a buffer containing an enzyme to the column.

5. The method of claim 3, wherein the the cell capture layers comprise beads conjugated with antibodies against CD31 and CD144 above beads conjugated with antibodies against CD34.

* * * * *